United States Patent [19]

Miskew

[11] 4,274,401
[45] Jun. 23, 1981

[54] APPARATUS FOR CORRECTING SPINAL DEFORMITIES AND METHOD FOR USING

[76] Inventor: Don B. W. Miskew, 422 Ridge Ave., Winnetka, Ill. 60093

[21] Appl. No.: 967,599

[22] Filed: Dec. 8, 1978

[51] Int. Cl.³ .............................................. A61F 5/00
[52] U.S. Cl. ................................... 128/69; 128/92 R
[58] Field of Search ..................... 128/68, 69, 75, 78, 128/92 R, 92 A, 92 B, 92 E, 84 B; 3/1.9; 85/32 V

[56] References Cited

U.S. PATENT DOCUMENTS

| 752,074 | 2/1904 | Jackson | 85/32 V |
|---|---|---|---|
| 2,774,350 | 12/1956 | Cleveland | 128/92 R |
| 3,242,922 | 3/1966 | Thomas | 128/92 R |
| 3,565,065 | 2/1971 | Roaf | 128/69 |
| 4,078,559 | 3/1978 | Nissinen | 128/69 |
| 4,085,744 | 4/1978 | Lewis et al. | 128/69 |
| 4,112,935 | 9/1978 | Latypov et al. | 128/69 |

FOREIGN PATENT DOCUMENTS

| 2649042 | 5/1978 | Fed. Rep. of Germany | 128/92 B |
|---|---|---|---|
| 2151475 | 4/1973 | France | 128/69 |
| 2244446 | 11/1977 | France | 128/69 |
| 569359 | 5/1945 | United Kingdom | 85/32 V |
| 485739 | 12/1975 | U.S.S.R. | 128/69 |

OTHER PUBLICATIONS

*Harrington* (R); Harrington Spine Instrumentation & Fusion Techniques, Zimmer Catalog - 1973 - Warsaw, Indiana.
*Zielke;* Ventrole Derotationsspondylodese; Arch Orthop. Unfall–Chir 85, 257–277, (1976).
*Zielke;* Ventrole Derotationsspondylodese; Orthopaedische Praxis, Heft 8, 1975, pp. 562–569.
*Armstrong* et al.; A Transverse Loading System Applied to a Modified Harrington Inst.; Clinical Orthopaedics & Related Research, #108, May 1978, Submitted by Applicant.
*Dwyer;* Instrumentation for Dwyer Spinal Technique; Zimmer Catalog - No date, Submitted by Appl.
*Herrmann;* Metal Plate Fixation . . . Cervical Spine; Acta Neurochirurgica 32, 101–111, (1975), Submitted by App.
*Weiss;* Weiss Springs - pp. 33, 35, Zimmer Catalog, No date - Submitted by App.
*Harrington* (U); Harrington Distraction System; pp. 2–5, Zimmer Catalog - No date, Submitted by App.
*Moe;* Moe Spinal Instrumentation; p. 14, Zimmer Catalog - No Date, Submitted by Applicant.
*Leatherman;* Leatherman Spinal Instrumentation, p. 17, Zimmer Catalog - No Date, Submitted by App.
*Knodt;* Knodt Distraction-Fusion Instrumentation, p.26 – Zimmer Catalog - No Date, Submitted by App.
*Andre;* Andre Spinal Instrumentation; p. 18 of Zimmer Catalog - No Date, Submitted by App.
*Andre;* Andre Spinal Instrumentation, p. 18, Zimmer Catalog, No Date, Submitted by Applicant.
*Cotrel D. T. T.;* Cotrel D. T. T. System; Adin J. of Bone & Joint Surgery - Sep. 78.

Primary Examiner—Robert W. Michell
Assistant Examiner—Arthur S. Rose
Attorney, Agent, or Firm—Wendell E. Miller

[57] ABSTRACT

The present invention provides an apparatus for use in the correction of spinal deformities, such as scoliosis, by posterior surgical procedures. It has been a problem to achieve secure hooking attachment to either laminae or transverse processes due to transverse and angular displacements of the individual vertebrae; and it has been a problem to provide adequate rotational forces for correction of rotational deformities. The present invention solves these problems by the use of a carrier (88) and a hook (90) that is attached to the carrier (88) by a spherical surface (102) of an attaching portion (100), and by the use of an angular pull carrier (182) that increases the rotational correcting force of a hook (90). The principle uses of the invention include orthesis and prosthesis.

34 Claims, 46 Drawing Figures

FIG. 4     FIG. 2
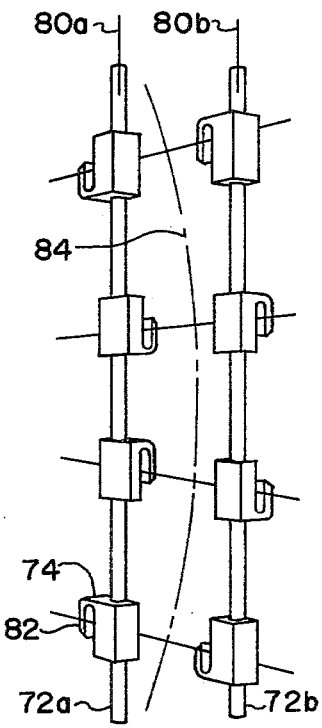
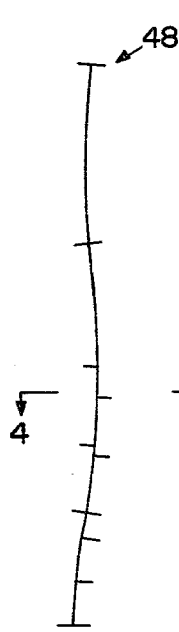
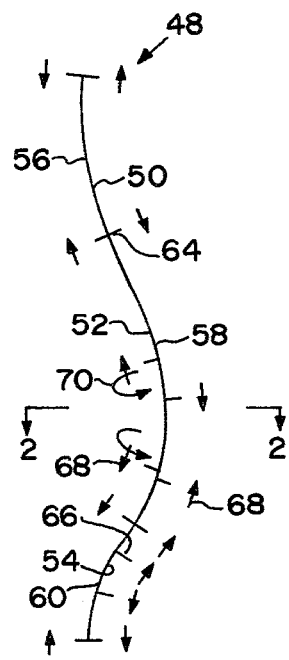
FIG. 3     FIG. 1     FIG. 7
PRIOR ART
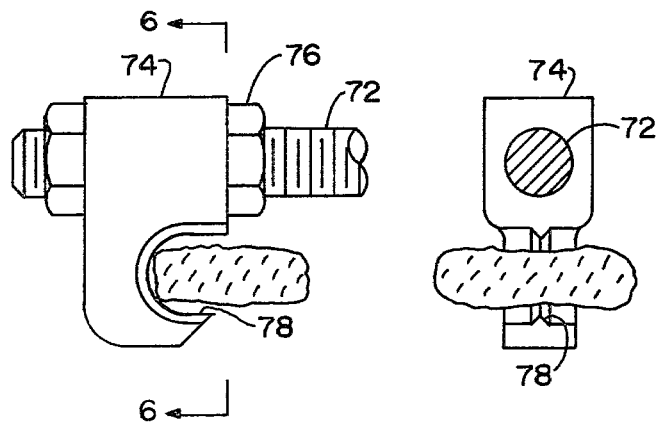
FIG. 5
PRIOR ART
FIG. 6
PRIOR ART
FIG. 8
PRIOR ART

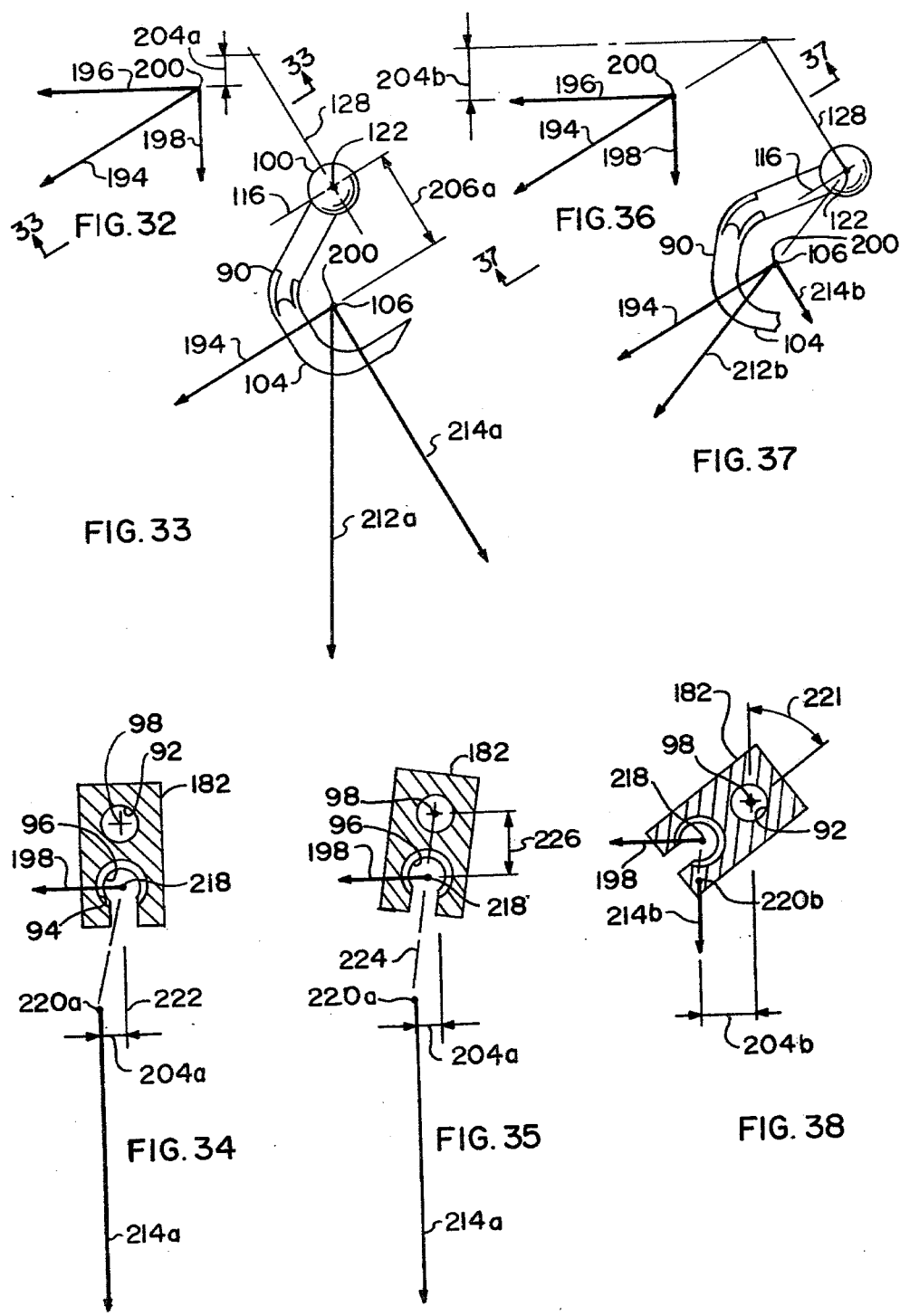

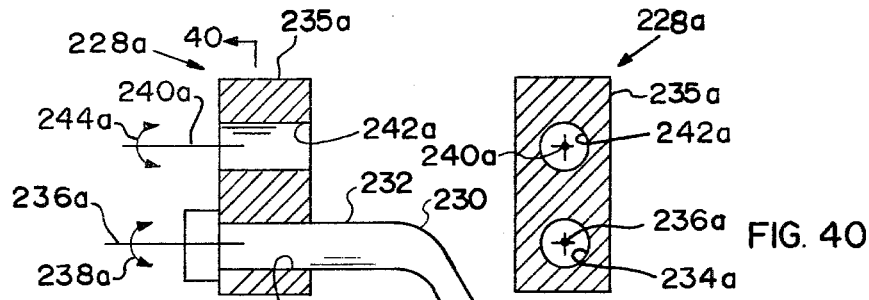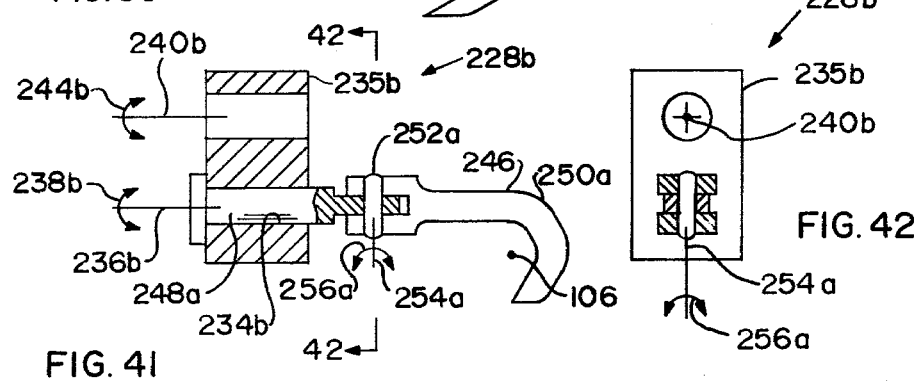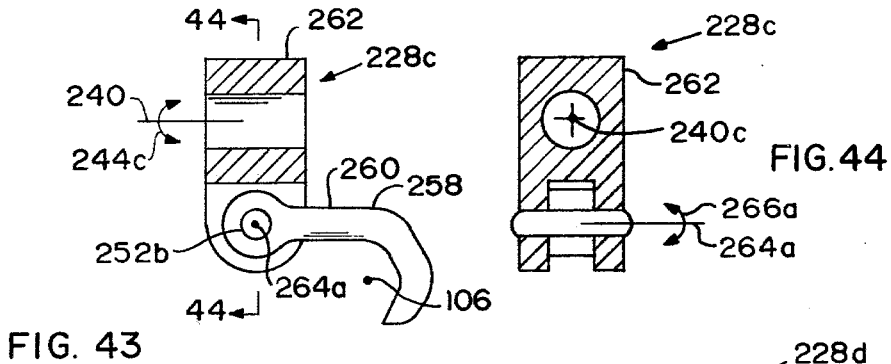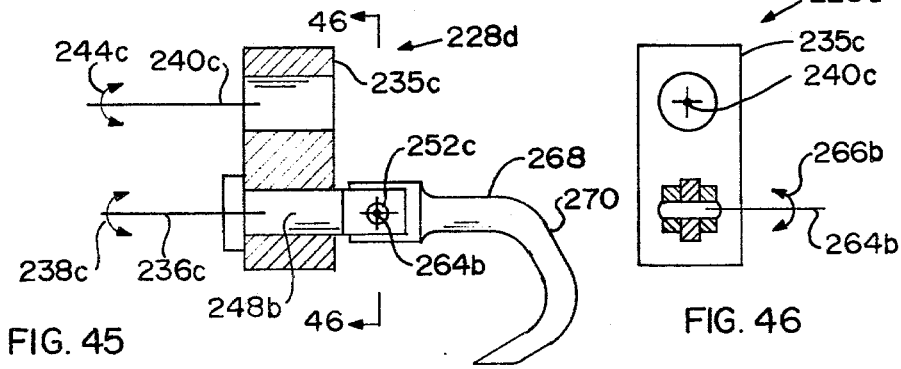

APPARATUS FOR CORRECTING SPINAL DEFORMITIES AND METHOD FOR USING

TECHNICAL FIELD

The present invention relates generally to apparatus and methods for correcting spinal deformities, and more particularly to apparatus and methods for correcting scoliosis and spinal fractures by posterior surgical procedures.

BACKGROUND ART

Correction of spinal deformities, such as scoliosis, kyphosis, and spinal instability, has utilized external traction apparatus, external bracing devices, external frameworks that extend inwardly of the patient's body and attach to vertebrae as taught by Latypov in U.S. Pat. No. 4,112,935, and apparatus for implantation into the patient's body for orthesis and/or prosthesis.

Implantation apparatus has included apparatus for anterior implantation and apparatus for posterior implantation.

Another implantation has included that known by the trade name Dwyer in which screws with transversely disposed holes in the heads thereof are anteriorly screwed into the body of various ones of the vertebrae. A wire or cable is threaded through the holes in the screw hands and tensioned to produce a compressive and stabilizing force.

Posterior implantation apparatus has included that taught by Roaf, U.S. Pat. No. 3,565,066, in which a rigid member bridges a scoliotic, kyphotic, or lordotic curve and hooks are disposed orthogonally to the rigid member and are used to hookingly engage and to move individual vertebrae toward the rigid member.

Posterior implantation apparatus has also included Nissinen, U.S. Pat. No. 4,078,559, in which a rigid and longitudinally extendable rod is used to tension a pair of flexible rods that are parallel disposed to the rigid rod. A plurality of wire loops engage transverse processes on the convex side of a scoliotic curve and also engage a proximal one of the flexible rods. Tensioning of the flexible rods by the rigid rod produces a straightening force on the flexible rods and results in a straightening force on the vertebrae by means of forces exerted by the wire loops.

Posterior implantation apparatus has further included helical coil tension springs whose ends are connected to respective ones of vertebrae by metal hooks. This type of apparatus is known by the trade name Weiss and provides a degree of fixation for fractures and fracture dislocations of the spine.

The posterior implantation apparatus that has gained the greatest acceptance in that which comprises an elongated and rigid rod and two or more hooks that are hooked onto respective vertebrae and that are secured to the rigid rod. A pair of rods may be used with one rod and the hooks thereof providing a distraction force and the other rod and the hooks thereof providing a compression force. This general type of apparatus has been sold under various trade names but primarily under the trade name Harrington.

Finally, the prior art includes Lewis et al., U.S. Pat. No. 4,085,744, in which a plurality of flat straps are alternately interconnected by engagement of hook shanks and adjusting devices. The hooks may be connected to individual vertebrae for applying distraction or compression forces.

DISCLOSURE OF INVENTION

In accordance with the broader aspects of this invention, there is provided an apparatus for use in correction of spinal deformities by posterior surgical procedures, which apparatus comprises an elongated and threaded rod having a longitudinal axis, first and second carriers, first and second hooks, and a plurality of threaded nuts.

The carriers each include a rod-receiving opening therethrough, are each assembled onto the elongated rod, and each include a concave spherical socket that is radially displaced from the longitudinal axis of the elongated rod and that is substantially planar and parallel thereto.

The hooks each comprise an attaching portion that includes a convex spherical surface, a hooking portion that is disposed around a hook axis and that opens toward the attaching portion, and a hook shank that interconnects the attaching portion and the hooking portion.

Pairs of the threaded nuts are assembled onto the elongated rod on opposite sides of respective ones of the rod-receiving openings of the carriers and are adjusted to move respective ones of the carriers and hooks.

The carriers and hooks may be assembled to the elongated rod with the hooks opening toward each other to provide compression forces or with the hooks opening distal from each other to provide distraction forces. Preferably, one elongated rod, four carriers, and four hooks are used in distraction on the concave side of the scoliotic curve. Also, preferably, a second elongated rod, four carriers, and four hooks are used in compression on the convex side of the scoliotic curve.

The hooks are each rotatably positionable about the longitudinal axis of respective ones of the elongated rods and are also rotatably positionable about a pivot axis or second longitudinal axis that is parallel to the longitudinal axis of the respective elongated rod and that intercepts the attaching portion of the respective hook. Thus the attaching portion of each hook is transversely positional with respect to the longitudinal axis of the rod to which it is attached and with respect to the spine. This allows the hook and the attaching portion thereof to be transversely positioned to provide source attachment to the laminae of the spine even when large transverse deviations of the laminae occur over the length of the elongated rod.

This ability to transversely position the hooks and the attaching portions thereof also allows the hooks of a given rod to be positioned for attachment to both laminae and transverse processes on a given side of the spinous processes.

Since the attaching portions of the hooks are secured to the carriers in a spherically radiused socket, the hooks are pivotable around three axes which intercept the attaching portions of the hooks. This freedom of movement in three planes allows a hook to be positioned to firmly seat against a bone surface even though that bone surface is not orthogonal to the longitudinal axis of the rod; and, when dealing with scoliotic spines, it is apparent that the hooking surfaces of nearly every lamina and transverse process are at some angle other than orthogonal with respect to the longitudinal axis of the rod.

Another advantage of the present invention and the means of attaching the hooks thereof is that, during straightening, the hooks self-align in the spherical surfaces of the carriers to maintain secure attachment to the respective vertebrae as the scoliotic curve is removed.

A further advantage of the present invention is that the elongated rod may be transversely and posteriorly positioned with respect to the spinous processes and transverse processes before the straightening process for best attachment to all hooks and then may be repositioned within the posterior confines of the spinous processes after the straightening process is completed. This positioning of the elongated rods is accomplished by rotating the carriers around the longitudinal axes of the elongated rods and by rotating the carriers around respective ones of the attaching portions of the hooks.

Because of the unique method of attaching the hooks to the elongated rods by means of the carriers and threaded nuts, it is possible to space the hooks as close as 2.5 centimeters. Thus it is possible to use a plurality of attaching points to the vertebrae to better distribute the distraction and compression forces.

In addition, because of the aforementioned ability to transversely position the hooks, it is possible to use a plurality of hooks that are uniformly distributed along the elongated rod; whereas, in the prior art, the variations in the transverse distances from the elongated rod to the various attachment points of the spine have prevented the use of more than two hooks per rod except where additional hooks have been placed in close longitudinal proximity to the ends of the rod.

Freedom of the hooks to pivot about a pivot axis, that is provided by the spherical surface attachment of the hooks, that is parallel to the hooking axis of the hooks and orthogonal to the longitudinal axis of the elongated rod, causes the hooking portion of the hooks to pivot toward longitudinal alignment with the attaching portion of the respective one of the hooks, thereby pivoting the point of each hook away from the spinal cord when attachment is made into the laminae and hooking forces are applied. Thus the present invention provides a degree of safety from accidental damage to the spinal cord.

This freedom of movement of the hooks about a pivot axis and the pivotal movement of the hooking portion about the pivot axis in response to the application of longitudinal forces is also used to apply rotational forces to correct rotational deformities of the scoliotic spine.

For the correction of rotational deformities, angular pull carriers are provided for attachment to the transverse processes; and the angular pull provides secure attachment to the transverse processes.

When the angular pull carrier is used, and a pulling force is applied to the hook that is attached thereto, the pull of the hook rotates the carrier in the direction that moves the attaching portion of the hook posteriorly, thereby providing additional rotational correction to the vertebrae.

These and other features and advantages of the present invention will be readily apparent when referring to the following detailed description wherein specific ones of like parts are separately distinguished by addition of a suffix letter to the part number thereof and wherein:

BRIEF DESCRIPTION OF DRAWINGS

FIG. 1 is a schematic and posterior view of a scoliotic spine;

FIG. 2 is a cross-sectional view of the scoliotic spine of FIG. 1 taken substantially as shown by section line 2—2;

FIG. 3 is a schematic and posterior view of the scoliotic spine of FIG. 1 after correction by use of the apparatus of the present invention;

FIG. 4 is a cross-sectional view of the spine of FIG. 3 taken substantially as shown by section line 4—4;

FIG. 5 is a side elevation of a prior art device showing one hook attached to a portion of the threaded rod thereof;

FIG. 6 is a view of the prior art apparatus of FIG. 5 taken substantially as shown by section line 6—6 of FIG. 5;

FIG. 7 is a schematic view depicting the inadequacies of the prior art device of FIGS. 5 and 6 in achieving secure attachment to a scoliotic spine;

FIG. 8 is a view similar to that of FIG. 6 showing the angular and insecure attachment that is achieved when attempting to make hooking connections to a scoliotic spine as schematically depicted in FIG. 7;

FIG. 32 is a top view of a force vector diagram for the embodiment of FIG. 29;

FIG. 33 is a side elevation of a hook, taken substantially as shown by view line 33—33 of FIGS. 29 and 32, and showing force vectors thereupon before the hook rotates upwardly due to the longitudinal hooking force thereupon;

FIG. 34 is a cross-sectional view of the angular pull carrier, taken as shown by section line 34—34 of FIG. 30 and showing force vectors thereupon before rotation of the carrier by the force vectors;

FIG. 35 is a cross-sectional view similar to that of FIG. 34 but showing rotation of the carrier due to the downward pull of the vertical pull force vector;

FIG. 36 is a top view of the force vector diagram after the hook has rotated upwardly;

FIG. 37 is a side elevation of the hook, taken substantially as shown by view line 37—37 of FIG. 36, and showing force vectors thereupon after the hook has rotated upwardly due to the longitudinal hooking force thereupon;

FIG. 38 is a cross-sectional view similar to that of FIG. 34 but showing resultant rotation thereupon by all hooking forces of the vector diagrams in FIGS. 36 and 37;

FIG. 39 is a cross-sectional view of a first alternate hook and carrier subassembly;

FIG. 40 is a cross-sectional view of the hook and carrier subassembly of FIG. 39, taken substantially as shown by section line 40—40;

FIG. 41 is a cross-sectional view of a second alternate hook and carrier subassembly;

FIG. 42 is a cross-sectional view of the hook and carrier subassembly of FIG. 41, taken substantially as shown by section line 42—42;

FIG. 43 is a cross-sectional view of a third alternate hook and carrier subassembly;

FIG. 44 is a cross-sectional view of the hook and carrier subassembly of FIG. 43, taken substantially as shown by section line 44—44;

FIG. 45 is a cross-sectional view of a fourth alternate hook and carrier subassembly; and FIG. 46 is a cross-sectional view of the hook and carrier subassembly of FIG. 45, taken substantially as shown by section line 46—46.

BEST MODE FOR CARRYING OUT THE INVENTION

Figures 9, 10:
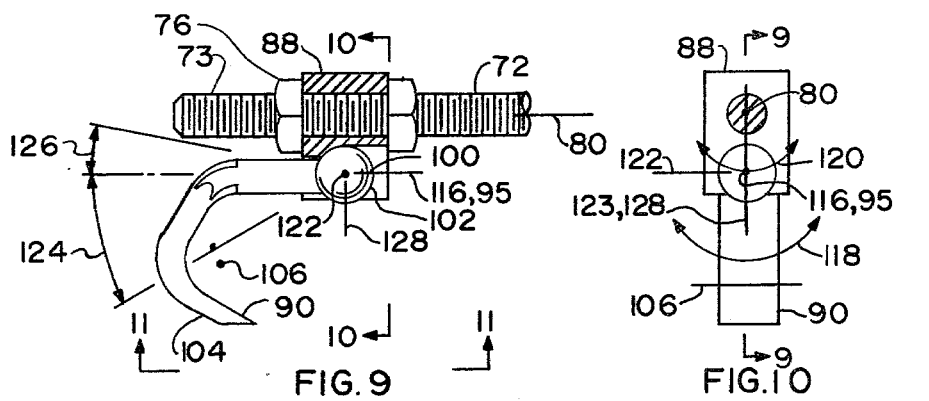
FIG. 9 is a cross-sectional view taken substantially as shown by section line 9—9 of FIG. 10 and depicting the preferred embodiment of the present invention.
FIG. 10 is a view of the preferred embodiment of FIG. 9, taken substantially as shown by section line 10—10 of FIG. 9.

Referring now to the drawings, and more particularly to FIGS. 1-4, a scoliotic spine 48 includes concave curves 50, 52, and 54 and convex curves 56, 58, and 60. The scoliotic spine 48 also includes a rotational deformity as shown by a vertebra 62 in FIG. 2.

FIG. 3 shows substantial correction of the aforementioned curves of the spine 48 and also shows that the rotational deformity, as shown by the vertebra 62 in FIG. 2, has been corrected, as shown in FIG. 4.

Referring again to FIG. 1, transverse lines, generally numbered 64, intercept and cross the spine 48 at locations wherein inflection points of the curves 50, 52, and 54 occur. In addition, transverse lines, generally numbered 66, project orthogonally outward from various points along the curves 52, 54, and 58. The purpose of the transverse lines 64 and 66 is to graphically illustrate the fact that, to obtain secure attachment of hooks to various vertebrae in a scoliotic spine, the hooks must have a pivotal axis of freedom wherein the hooks can pivot to orthogonally attach to surfaces which are represented by the transverse lines 64 and 66.

Again referring to FIG. 1, arrows, generally numbered 68, are used to illustrate compression and distraction forces which are to be applied to the scoliotic spine 48 to correct the scoliotic curves thereof. In addition, rotation arrows 70 are superimposed upon two of the arrows 68 to show that rotational correction forces are to be applied to two of the vertebrae that are schematically represented by the transverse lines 66 as well as applying distraction forces thereto.

Referring now to FIGS. 5 and 6, the most successful and most generally used prior art device has consisted of an elongated member or externally threaded and elongated rod 72 and two or more hooks, such as a hook 74. In the FIG. 5 embodiment, the hook 74 is longitudinally positioned along the elongated rod 72 by a pair of threaded nuts 76. The hooks of the type depicted by the hook 74 have optionally included a knife edge 78 inside the hook to achieve more secure hooking to the individual vertebra.

Referring now to FIG. 7, elongated rods 72a and 72b are shown equipped with a plurality of hooks, such as the hook 74 of FIGS. 5 and 6, and also generally numbered 74. The hooks 74 are shown rotationally positioned about longitudinal axes 80a and 80b of the elongated rods 72a and 72b in an attempt to transversely position hooking portions 82 of the hooks 74 at equal transverse distances from a scoliotic curve 84.

Referring now to FIG. 8, the rotational positioning of the hooks 74 of FIG. 7 results in angular engagement between a hook 74a of FIG. 8 and a vertebra portion 86a. Thus one of the problems of the prior art apparatus has been the inability to obtain secure hooking contact with various vertebrae due to the scoliotic curve of the spine.

Figure 11:
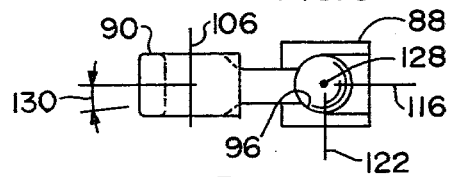
FIG. 11 is a bottom view of the preferred embodiment of FIG. 9, taken substantially as shown by view line 11—11 of FIG. 9.

Referring now to FIGS. 9-11, the preferred embodiment of the present invention includes a carrier, generally numbered 88, an elongated member or elongated rod 72, nuts 76, and a hook 90.

Figure 12:
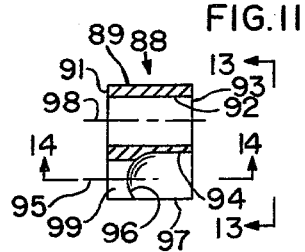
FIG. 12 is a cross-sectional view of the carrier of FIG. 9, taken substantially as shown in FIG. 9.
Figure 13:
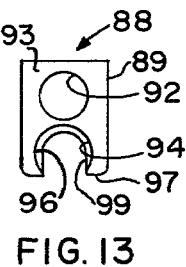
FIG. 13 is an end view of the carrier of FIG. 12 taken substantially as shown by view line 13-13 of FIG. 12.
Figure 14:
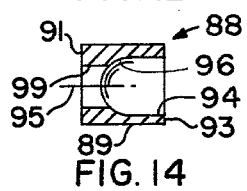
FIG. 14 is a cross-sectional view of the carrier of FIG. 12 taken substantially as shown by section line 14—14 of FIG. 12.

Referring now to FIGS. 12-14, the carrier 88 includes a carrier body 89 having end surfaces 91 and 93, having a rod-receiving opening 92 that is disposed along a longitudinal axis 98 and that intercepts the end surfaces 91 and 93. The carrier body 89 also includes a socket 94 that is radially displaced along an axis that is parallel to the rod-receiving opening 92. The socket 94 includes a concave spherical surface or socket surface 96 that is disposed between the surfaces 91 and 93 and that is substantially a surface of revolution about the socket axis 95.

The carrier body 89 includes a side surface 97 that is remote from the longitudinal axis 98, that is adjacent to the socket axis 95, and that interconnects the end surfaces 91 and 93; and the carrier body 89 includes a shank-receiving slot 99 that is disposed parallel to the socket axis 95, and that opens the socket 94 into both the end surface 91 and the side surface 97.

The concave spherical surface 96 is preferably centered 7.1 millimeters from the longitudinal axis 98 of the rod-receiving opening 92.

Referring now to FIGS. 9-14, the longitudinal axis 98 of the rod-receiving opening 92 substantially coincides with the longitudinal axis 80 of the elongated rod 72 when the carrier 88 is assembled onto the elongated rod 72. Thus, in the following discussion, reference to one of these longitudinal axes will be understood as also pertaining to the other of these axes.

Figures 15, 16:
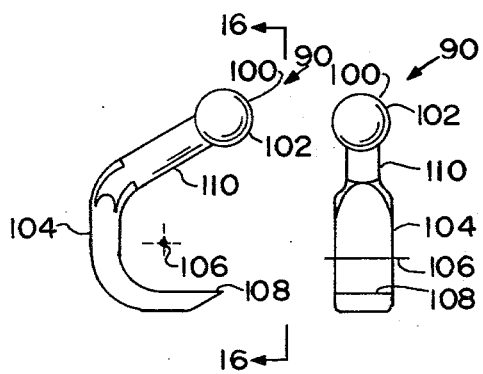
FIG. 15 is a side elevation of the preferred embodiment of the hook of the present invention.
FIG. 16 is an end view of the hook of FIG. 15, taken substantially as shown by view line 16—16 of FIG. 15.

Referring now to FIGS. 15 and 16, the hook 90 includes an attaching portion 100 that includes a convex spherical surface 102, a hooking portion 104 that opens toward the attaching portion 100, that is disposed around a hook axis 106 and that includes a hook point 108, and a hook shank 110 that interconnects the attaching portion 100 and the hooking portion 104.

The diameter of the attaching portion of the hook 90 is preferably 6.35 millimeters; and, since FIGS. 15 and 16 are drawn to scale, other preferred dimensions of the hook 90 can be determined by scaling the drawings.

Figures 17, 18:
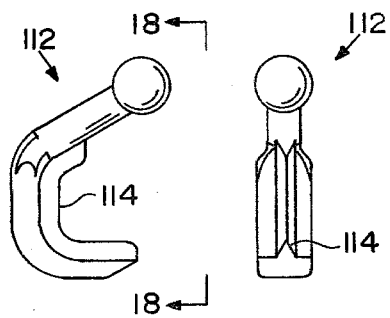
FIG. 17 is a side elevation of a hook similar to that of FIG. 15 but with a knife edge included inside the hooking portion thereof.
FIG. 18 is an end view of the hook of FIG. 17, taken substantially as shown by view line 18—18 of FIG. 17.

Referring now to FIGS. 17 and 18, a hook 112 is identical to the hook 90 of FIGS. 15 and 16 with the exception of the addition of a knife edge 114.

Referring now to FIGS. 9-14, the elongated rod 72 preferably includes an externally threaded portion 73 and has an outside diameter of 4.76 millimeters, and the rod-receiving opening 92 of the carrier 88 is sized for free longitudinal and rotational movement of the carrier 99 about the longitudinal axis 80 of the elongated rod 72.

Because of the spherical attachment of the hook 90 to the carrier 88 by means of the concave spherical surface 96 of the socket 94 and the convex spherical surface 102 of the attaching portion 100, the hook 90 is free to pivot about a pivot axis 116, that is radially displaced from but planar and parallel to the longitudinal axis 80, as depicted by arrows 118. In like manner, the attaching portion 100 of the hook 90 is free to pivot about the longitudinal axis 80 as depicted by arrows 120.

Also, because of the spherical surface attachment of the hook 90 to the carrier 88, the hook 90 is free to pivot about a pivot axis 122 that intercepts the attaching portion 100 and that is not only planar and spaced apart from the hook axis 106, but that is also orthogonal to the longitudinal axis 80; so that the hook 90 is free to pivot in a hooking plane 123 that includes both the longitudinal axis 80 and the socket axis 95.

The hooking portion 104 is free to pivot downwardly and away from the elongated rod 72 by an angle 124 which is drawn at 30 degrees although it is possible for the hooking portion 104 to rotate downwardly by 90 degrees. The hooking portion 104 is also free to pivot upwardly at an angle 126 which depends upon the design parameters but which is preferably at least 6 degrees.

Referring finally to FIGS. 9-14, the spherical attachment of the hook 90 to the carrier 88 by the spherical surfaces 96 and 102 also allows the hooking portion 104 to rotate about a pivot axis or transverse axis 128 that is orthogonal to and that intercepts the longitudinal axis 80 of the elongated rod 72. Preferably, the hooking portion 104 is free to pivot about the pivot axis 128 in each direction by an angle 130 which is at least 6 degrees.

Figure 19:
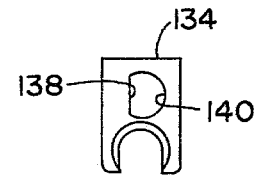
FIG. 19 is an end view of an alternate embodiment of the carrier of FIG. 13, showing a flattened rod-receiving opening therethrough.
Figure 20:
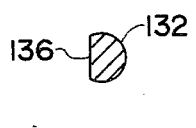
FIG. 20 is a cross-sectional view of an elongated rod showing a flattened portion that is adapted for use with the carrier of FIG. 19.

Referring now to FIGS. 19 and 20, it is contemplated that it may be desirable to predetermine the angular position between an elongated rod 132 and a carrier 134. Thus, in the alternate embodiment of FIGS. 19 and 20, a flat 136 of the elongated rod 132 mates with a flat 138 of a rod-receiving opening 140 in the carrier 134 to predetermine the rotational position of the carrier 134 with respect to the elongated rod 132.

Figure 21:
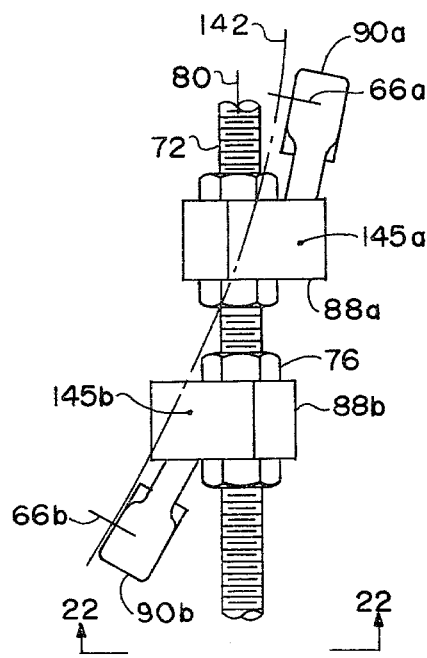
FIG. 21 is a posterior view showing rotational positioning of the carriers and pivoting of the hooks.
Figure 22:
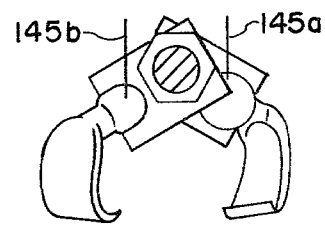
FIG. 22 is an end view of the apparatus of FIG. 21 taken substantially as shown by view line 22—22 of FIG. 21.

Referring now to FIGS. 21 and 22, carriers 88a and 88b are shown rotationally positioned about the longitudinal axis 80 of the elongated rod 72 to obtain transverse positioning of hooks 90a and 90b with respect to a scoliotic curve 142; and the hooks 90a and 90b are positioned about pivot axes 145a and 145b to achieve orthogonal engagement with hooking surfaces of vertebrae which are schematically depicted by transverse lines 66a and 66b.

Figure 23:
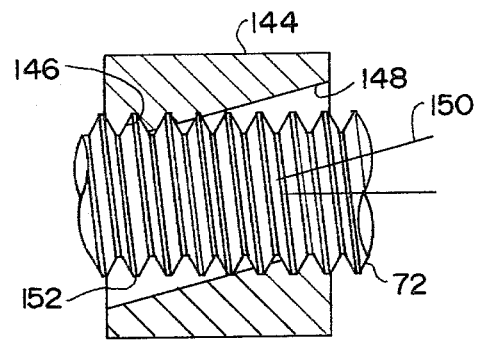
FIG. 23 is a cross-sectional view of the rod, and a threaded slide nut which may be alternately used to achieve rapid adjustment of the apparatus.
Figure 24:
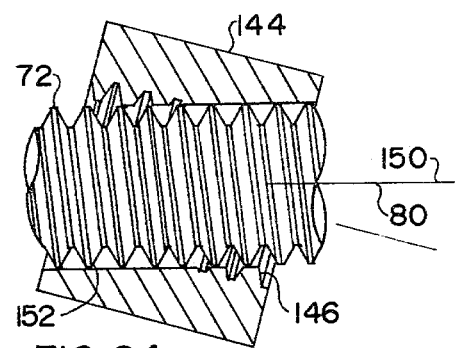
FIG. 24 is a cross-sectional view of the rod and nut of FIG. 23 with the nut shown in the sliding position.

Referring now to FIGS. 23 and 24, a threaded slide nut 144 includes internal threads 146 and an angularly inclined bore 148 that is inclined along a bore axis 150. In FIG. 24, the threaded slide nut 144 is shown rotated to an angle wherein the bore axis 150 coincides with the longitudinal axis 80 of the elongated rod 72. With the slide nut 144 inclined as shown in FIG. 24 it is possible to longitudinally position the slide nut 144 with respect to the elongated rod 72 without rotating the slide nut 144. However, when the slide nut 144 is positioned as shown in FIG. 23, the internal threads 146 of the slide nut 144 engage threads 152 of the elongated rod 72; and then the slide nut 144 may be rotated about the longitudinal axis 80 to produce translational movement of the slide nut 144. Thus the slide nut 144 of FIGS. 23 and 24 can be interchanged with nuts 76 of FIG. 21 to achieve rapid positioning of the carriers 88 along the elongated rod 72.

Figure 25:
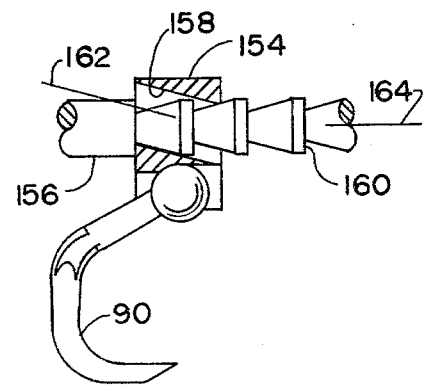
FIG. 25 is a cross-sectional view of a second alternate embodiment which may be used to achieve rapid adjustment of the apparatus.

Referring now to FIG. 25, a second alternate embodiment for achieving rapid positioning of a carrier 154 along an elongated rod 156 includes an angularly disposed bore 158 in the carrier 154 and a plurality of circumferentially disposed adjustment stop surfaces 160 on the elongated member or elongated rod 156. The carrier 154 may be positioned along the elongated rod 156 by rotating the carrier 154 to an angle wherein a bore axis 162 of the bore 158 coincides with a longitudinal axis 164 of the elongated rod 156.

Thus, the threaded slide nut 144 of FIG. 23 and the combination of the angularly disposed bore 158 and the adjustment stop surfaces 160 of FIG. 25 provide alternate means to the threaded nuts 76 for selectively adjusting the longitudinal positions of the carriers 88 and 154, and thereby for longitudinally positioning the hooks 90.

Figure 26:
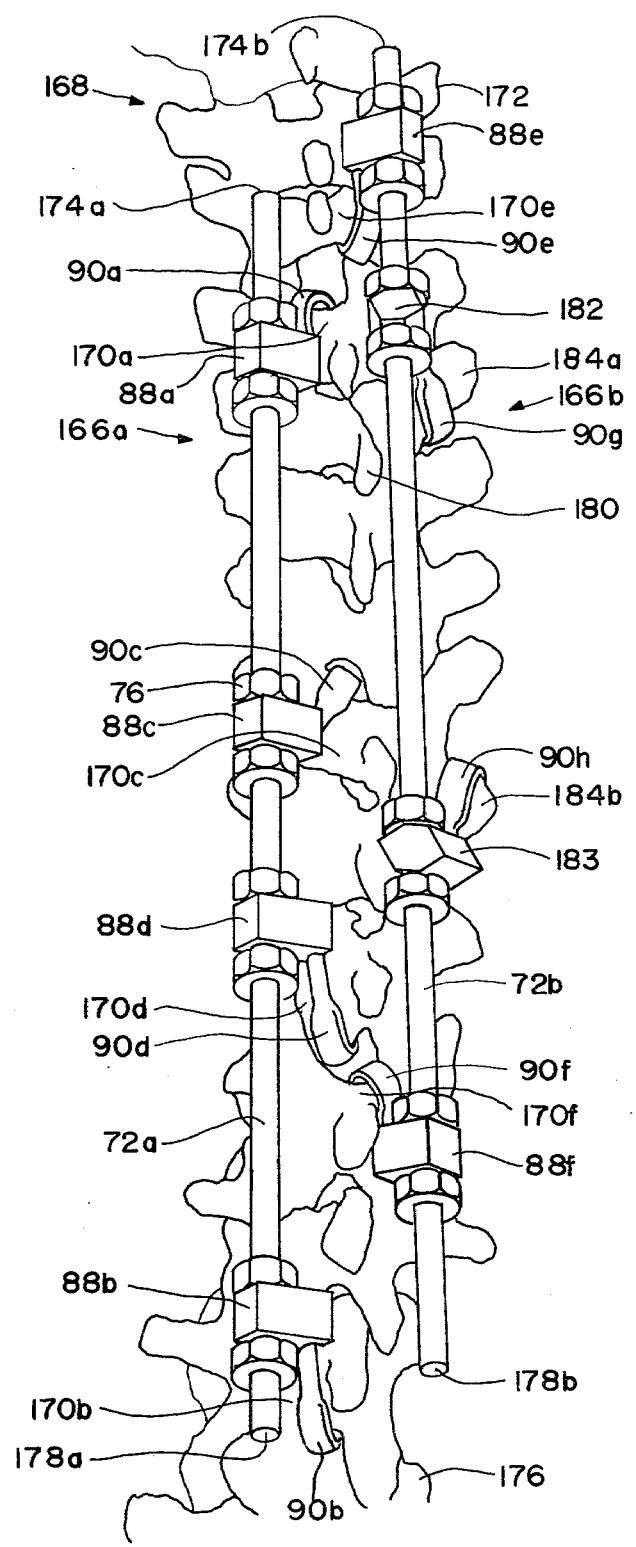
FIG. 26 is a perspective and substantially posterior view of a spine showing the apparatus of the present invention installed thereupon.

Referring now to FIG. 26, an apparatus 166a, which is made according to the teaching of the present invention, and which includes an elongated member or elongated rod 72a, four carriers 88a, 88b, 88c, and 88d, four hooks 90a, 90b, 90c, and 90d, and eight threaded nuts generally numbered 76, is shown attached to a spine 168.

The hook 90a is attached into a lamina 170a from the cephalad side thereof and proximal to the cephalad end 172 of the spine 168; and the hook 90a is proximal to an end 174a of the elongated rod 72a. The hook 90b is attached into a lamina 170b on the caudad side thereof proximal to a caudad end 176 of the spine 168 and proximal to an end 178a of the elongated rod 72a. Thus the hooks 90a and 90b apply a compressive force to the spine 168 on the side of the spinous processes 180 that lies leftwardly thereof as viewed in FIG. 4.

Referring again to FIG. 26, the hooks 90c and 90d are attached to respective ones of laminae 170c and 170d and are positioned to provide a compressive force on the spine 168 leftwardly of the spinous processes 180.

A second apparatus 166b includes a second elongated rod 72b that is positioned rightwardly of the spinous processes 180 and that includes a pair of carriers 88e and 88f that are proximal to respective ones of ends 174b and 178b of the elongated rod 72b. The hook 90e is hooked into a lamina 170e from the caudad side thereof; and the hook 90f is hooked into a lamina 170f on the cephalad side thereof proximal to the end 178b of the rod 72b. Thus the hooks 90e and 90f are positioned for applying a distractive force to the spine 168 on the side of the spinous processes 180 that lies rightwardly as shown in FIG. 26.

The apparatus 166b also includes angular pull carriers 182 and 183 and hooks 90g and 90h. The angular pull carrier 182 is positioned for pulling toward the cephalad end 172 of the spine 168 and the angular pull carrier 183 is positioned for pulling toward the caudad end 176 of the spine 168. Thus the angular pull carriers 182 and 183 are disposed for pulling away from each other, that is, for applying a distraction force to the spine 168.

The hooks 90g and 90h are attached to transverse processes 184a and 184b. The hooks 90g and 90h are used to provide a rotational correction for rotational deformities of the spine such as shown by the vertebra 62 of FIG. 2.

The unique method by which the hooks 90g and 90h and the angular pull carriers 182 and 183 provide a rotational as well as a longitudinal pull to the transverse processes 184a and 184b will be subsequently described.

Figure 27:
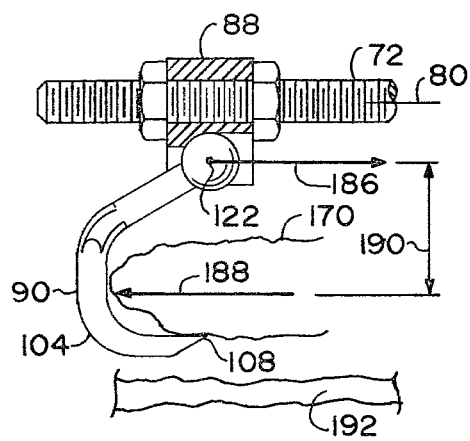
FIG. 27 is a cross-sectional view of a hook and carrier showing the angular position of the hook prior to applying a compression or a distraction force.
Figure 28:
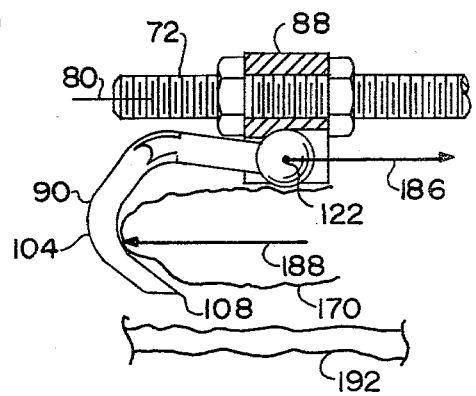
FIG. 28 is a cross-sectional view of a hook and carrier, showing the rotation of the hook and the hook point thereof away from the spinal cord when a force is applied to the hook.

Referring now to FIGS. 27 and 28, a hook 90 is hooked into a lamina 170 and a carrier 88 which is connected to the hook 90 is moved rightwardly exerting a force on the hook 90 that is indicated by a force vector 186. Movement of the carrier 88 rightwardly is opposed by the lamina 170 which applies a force to the hooking portion 104 of the hook 90 as indicated by a force vector 188 thereby producing a moment about the pivot axis 122 that is a function of the force vector 188 and a moment arm 190 that is the distance from the pivot axis 122 to the force vector 188 as measured orthogonally to the longitudinal axis 80 of the elongated rod 72.

The objective of the present discussion is to show that the hook point 108 of the hook 90, when the force of the vector 188 is applied, will be prevented from moving toward and damaging a spinal cord 192 by pivotal action of the hook 90 about the pivot axis 122.

Referring now to FIG. 28, application of the force vector 188 to the hooking portion 104 has resulted in clockwise rotation of the hook 90 in a hooking plane 193 around the pivot axis 122, tending to pull the hook point 108 away from the spinal cord 192 rather than forcing the hook point 108 toward the spinal cord 192.

Figure 29:
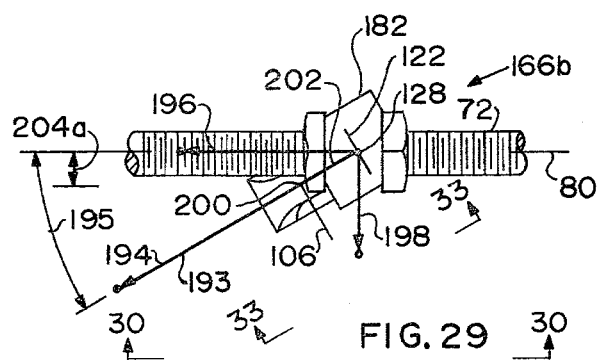
FIG. 29 is a top view of the embodiment of the present invention wherein an angular pull carrier is used, showing angular, longitudinal, and transverse force vectors.
Figure 30:
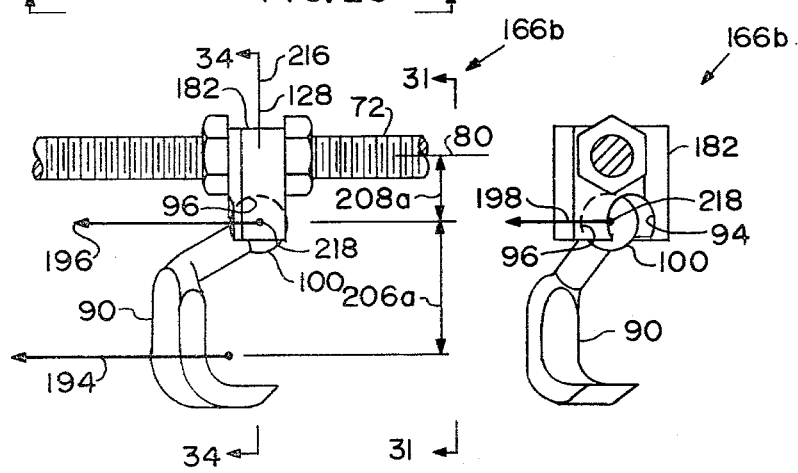
FIG. 30 is a side elevation of the embodiment of FIG. 29, taken substantially as shown by view line 30—30 of FIG. 29.
Figure 31:
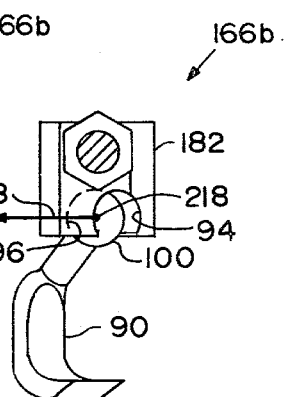
FIG. 31 is an end view of the embodiment of FIG. 29, taken substantially as shown by view line 31—31 of FIG. 30.

Referring to FIGS. 29-31, three views of a portion of the apparatus 166b are shown. Also, with the top view of FIG. 29, a force vector diagram is shown which includes a hooking force or angular pull force vector 194 that is rotated at an angle 195 that is preferably 30 degrees from the longitudinal axis 80 of the elongated rod 72 as seen in FIG. 29, a longitudinal force vector 196, and a transverse force vector 198. These vectors represent forces which are applied at a point 200 that represents an intersection of a centerline 202 of the hook 90 and the hook axis 106. The point 200 is transversely disposed in the top view of FIG. 29 by a distance 204a.

Referring now to FIGS. 9-11, 29-31, 33, and 37, the pivot axes 116, 122, and 128 maintain their respective parallel and orthogonal relationships to the hook axis 106 in all of the referenced figures; but the pivot axes 116 and 122 are rotated with respect to the longitudinal axis 80 by the angle 195 in FIGS. 29-31, 33, and 37 from their respective parallel and orthogonal relationships with the longitudinal axis 80 of FIGS. 9-11.

Referring now to FIGS. 32 and 33, the force diagram of FIG. 29 has been reproduced in modified form as FIG. 32; and the hook 90 of FIG. 29 has been shown as indicated by view line 33—33 of FIG. 29 with the angular pull force vector 194 applied to the hook axis 106.

Referring now to FIGS. 30 and 33, the angular pull force vector 194 is applied to the hook axis 106 at a distance 206a below the pivot axis 122 of the attaching portion 100. In like manner, the angular pull force vector 194 is applied at a distance below the longitudinal axis 80 of the elongated rod 72, as seen in FIG. 30, which is the sum of the distance 206a and a distance 208a, the distance 208a being the center distance between the longitudinal axis 80 of the elongated rod 72 and the pivot axis 122 of FIG. 33.

Referring again to FIG. 33, since any force applied to the spherically attached hook 90 must be applied through the pivot axis 122, the angular pull force vector 194 includes a hook centerline force vector 212a and a vertical pull force vector 214a. That is, for a force vector of the magnitude of the angular pull force vector 194 there is a vertical pull force vector of the magnitude indicated by the vertical pull force vector 214a.

Referring now to FIG. 34, a cross-sectional view of the angular pull carrier 182 of FIG. 30 is taken in a plane 216 (FIG. 30) which is orthogonal to the longitudinal axis 80 of elongated rod 72 and which intercepts a center 218 of the concave spherical surface 96. The transverse force vector 198 of FIGS. 29, 31, and 32 is applied through the center 218 (FIG. 34) of the concave spherical surface 96; and the vertical pull force vector 214a of FIG. 33 is applied at a point 220a (FIG. 34) which is transversely disposed from a centerline 222 by the distance 204a of FIGS. 29 and 32.

Referring now to FIGS. 34 and 35, the vertical pull force vector 214a is effective to rotate the angular pull carrier 182 clockwise about the longitudinal axis 98 of the rod-receiving opening 92 from the initial position as shown in FIGS. 29 and 34 to the angle wherein a pull line 224 of FIG. 35 intercepts the longitudinal axis 98, the center 218, and the point 220a. The transverse force vector 198 which is applied to the center 218 of the concave spherical surface 96 at a distance 226 from the longitudinal axis 98 will rotate the angular pull carrier 182 clockwise from the rotational position shown in FIG. 34 to the rotational position shown in FIG. 35.

Referring now to FIGS. 36 and 37, these two figures are similar respectively to FIGS. 32 and 33. The angular pull force vector 194, the longitudinal force vector 196, and the transverse force vector 198 remain as shown in FIG. 32, having the same magnitude as the like-numbered force vectors in FIG. 32; but the distance 204a of FIG. 32 increases to a distance 204b of FIG. 36 because of the upward swinging of the hook 90 as shown in FIG. 37.

The angular pull force vector 194 of FIG. 37 remains the same magnitude as the same-numbered force vector in FIG. 33; but the upward swinging of the hook 90 of FIG. 37 results in a substantial decrease in the magnitude of a hook centerline force vector 212b in FIG. 37 over the hook centerline force vector 212a in FIG. 33 and also results in a large reduction in a vertical pull force vector 214b in FIG. 37 as opposed to the vertical pull force vector 214a in FIG. 33.

Referring now to FIGS. 37 and 38, and more particularly to FIG. 38, application of the vertical pull force vector 214b at a point 220b, and application of the transverse force vector 198 at the center 218, results in clockwise rotation of the angular pull carrier 182 about the longitudinal axis 98 to an angle 221 that is in the order of 55 degrees.

Thus, when a hook 90, such as the hook 90h of FIG. 26, is hooked onto a transverse process, such as the transverse process 184b, the hook 90 is effective to rotate the respective vertebrae by pulling the respective transverse processes posteriorly because of two phenomena which have been previously described. One is the phenomenon of the rotation of the hook 90 about a pivot axis 122 as shown in FIGS. 27, 28, 33, and 37 that is a function of the vertical pull force vector 214a (FIG. 33) and the reduction in the vertical pull force vector 214b (FIG. 37) as rotation of a transverse process is accomplished. The second is the rotation of the angular pull carrier 182 about the longitudinal axis 98 as shown in FIG. 38. In other words, the hook axis 106 as shown in FIGS. 33 and 37 moves upwardly or posteriorly in response to an angular pull force vector 194 as shown in FIGS. 33 and 37; and the attaching portion 100 of the hook 90 of FIGS. 33 and 37 is moved upwardly or posteriorly by rotation of the angular pull carrier 182 as shown in FIG. 38. The combination of these two phenomena are uniquely effective in correcting rotational deformities of the spine as schematically indicated by the vertebra 62 in FIG. 2.

Referring now to FIGS. 12–14, 26, and 29–31, the angular pull carriers 182 and 183 of FIGS. 26, 29–31, 34, 35, and 38 are preferably constructed in accordance with the details for the carrier 88 as shown in FIGS. 12–14; except that, the socket 94 and the concave spherical surface 96 thereof of the angular pull carrier 182 of FIGS. 29–31 is inclined at an angle of 30 degrees with respect to the longitudinal axis 80 of the elongated rod 72 as shown by an angle 195, whereas the socket 94 and the concave spherical surface 96 of the carrier 88 of FIGS. 12–14 are both parallel and planar to the longitudinal axis 98 of the rod-receiving opening 92.

Having fully described the operation of the angular pull carrier 182 by the use of force vectors in FIGS. 29–38, it may be helpful to those who are unaccustomed to vector analysis to summarize the foregoing discussion in a less technical manner. Referring to FIGS. 29 and 30, the center 218 of the concave spherical surface 96 (FIG. 30) is below the axis 80 of FIG. 29; so pulling on the center 218 (FIG. 30) at the angle 195 (FIG. 29) by a hooking force 194 is effective to exert a rotational force on the carrier 182 that is a function of the hooking force 194, the angle 195, and the distance 208a (FIG. 30).

Again summarizing with regard to the angular carrier 182, there are three previously stated facts with regard to the carrier 88 of FIGS. 9–14, the carrier 182 of FIGS. 29–31, and the force vectors of FIG. 29 that need to be remembered. First of all, the hooking force for the angular carrier is preferably at an angle 195 (FIG. 29) of 30 degrees. Secondly, the carriers 88 (FIGS. 9–14) and 182 (FIGS. 29–31) are substantially the same except for the angular displacement of the socket 94 and the spherical surface 96 thereof. Thirdly, the angle 130 (FIG. 11) at which the hook 90 can rotate about the pivot axis or transverse axis 128 from the axis 116, is stated as being preferably at least six degrees.

From these three facts that have been restated in the preceding paragraph, it is obvious that the carrier 88 (FIGS. 9–14) will allow a hooking angle (195 of FIG. 29) of only 6 degrees or so from the longitudinal axis 80, and this relatively small angle would not only severely limit the magnitude of the transverse force vector 198, but it would also prevent achieving the aforestated desirable angle of 30 degrees for the angle 195 of FIG. 29. Thus in order to position the hook 90 at the angle 195 (FIG. 29), the socket 94 (FIG. 31) of the carrier 182 (FIGS. 29–31) must be at an angle which is at least equal to the desired hooking angle 195 (FIG. 29) less the angular freedom of the hook 90 as shown by the angle 130 (FIG. 11). Therefore, inclining the socket 94 at 30 degrees provides the desired hooking angle of 30 degrees with 6 degrees of freedom to spare.

Referring now to FIGS. 26 and 29, the angular pull carriers 182 and 183 differ only in that they are mirror images of each other as can be seen in FIG. 26.

Referring now to FIGS. 39–46, four alternate embodiments of a hook and carrier subassembly are shown which each achieve some of the features and advantages of a hook and carrier subassembly comprising the carrier 88 and the hook 90 of FIGS. 9–11.

Referring now to FIGS. 39 and 40, a hook and carrier subassembly 228a includes a hook 230 having an integral and cylindrical attaching portion 232 that is rotatably inserted into a cylindrical bore 234a of a carrier 235a. The hook 230 is rotatable about a pivot axis 236a as shown by arrows 238a; and the hook 230 is rotatable about a longitudinal axis 240a of a rod-receiving opening 242a as shown by arrows 244a. Thus the embodiment of FIGS. 39 and 40 is effective to overcome the deficiencies of the prior art embodiment of FIGS. 5 and 6 as shown in FIG. 8.

Referring now to FIGS. 41 and 42, a hook and carrier subassembly 228b includes a hook 246 having a separate attaching portion 248a that is pivotally connected to a hooking portion 250a by a pin 252a. The pin 252a includes a pivot axis 254a that is orthogonal to a hook axis 106; so that the hooking portion 250a is free to pivot about the pivot axis 254a as shown by arrows 256a.

The attaching portion 248a is rotatably journaled in a cylindrical bore 234b of a carrier 235b; so that, in addition to the hooking portion 250a being free to rotate about a pivot axis 254a as shown by arrows 256a, the hook 246 is free to pivot about the pivot axes 236b and 240b as shown by arrows 238b and 244b.

Thus, the embodiment of FIGS. 41 and 42 is effective to overcome the problem of the hook 74 needing to move transversely to make hooking connections to a scoliotic curve 84 of a spine as shown in FIG. 7, and also to achieve substantially orthogonal hooking engagement with the various vertebrae which are schematically indicated by transverse lines 64 and 66 of FIG. 1 as opposed to the angular and inadequate hooking of the prior art as shown in FIG. 8. In addition, the hook and carrier subassembly 228b of FIGS. 41 and 42 is able to swivel about the pivot axis 254a to hook to a selected vertebra orthogonally to the scoliotic curve 142 at any location therealong in the same manner as is achieved by the preferred embodiment as shown in FIGS. 21 and 22 and as indicated by the transverse lines 66a and 66b of FIG. 21.

Referring now to FIGS. 43 and 44, a hook and carrier subassembly 228c includes a hook 258 having an integral attaching portion 260 that is attached to a carrier 262 by a pin 252b; so that the hook 258 and a hook axis 106 thereof are free to pivot about a pivot axis 264a as shown by arrows 266a. The hook 258 is also free to pivot about a longitudinal axis 240c as shown by arrows 244c.

Thus the alternate embodiment of FIGS. 43 and 44 is able to achieve the advantage of the preferred embodiment as indicated in FIGS. 27 and 28 wherein a hooking force, as indicated by the force vector 188, which is applied to the hook 90, is effective to pull the point 108 of the hook 90 outwardly in response to the hooking force of the force vector 188 of the lamina 170, thereby avoiding damage to the spinal cord 192.

Referring now to FIGS. 45 and 46, a hook and carrier subassembly 228d includes a carrier 235c and a hook 268. The hook 268 includes an attaching portion 248b and a hooking portion 270 that are pivotally connected by a pin 252c; so that the hooking portion 270 is free to pivot about a pivot axis 264b as shown by arrows 266b. Thus the embodiment of FIGS. 45 and 46 includes the advantages of the embodiment of FIGS. 39 and 40 in that the hook 268 is free to pivot around pivot axes 236c and 240c as shown by arrows 238c and 244c respectively and includes the advantages of the embodiment of FIGS. 43 and 44 in that the hooking portion 270 is free to pivot about the pivot axis 264b; but the embodiment of FIGS. 45 and 46 does not achieve the pivotal freedom as provided by the pivot axis 128 of the preferred embodiment as shown in FIGS. 9 and 11.

In summary, the preferred embodiment of FIGS. 9-16, 21-22, and 26-38 provides a new and unique apparatus which achieves more secure hooking attachment to both laminae and transverse processes than prior art apparatus, which provides a larger number and more uniformly spaced hooking attachments for a higher degree of correction of scoliotic curves than prior art apparatus, which provides more rotational correction by the use of the angular pull carrier than prior art apparatus, and which tends to avoid damage to the spinal cord as another advantage over prior art apparatus.

The alternate embodiments of FIGS. 39-46 each achieve some of the aforementioned advantages over prior art apparatus while failing to achieve all of the aforementioned advantages of the preferred embodiment.

While there have been described above the principles of the present invention in connection with specific apparatus, and while numbers have been inserted into the appended claims in parentheses in connection with elements recited therein, it is to be clearly understood that both the description and the parenthetically included numbers are made only by way of example; and the scope of the invention is to be defined by the appended claims without limitation by the parenthetical numbers included therein.

Industrial Applicability

The apparatus and methods of the present invention provide new, unique, and useful advantages over prior art apparatus and methods not only for the correction of spinal curvature deformities such as scoliosis but also for spinal fracture deformities that require apparatus for immobilization, for deterioration or growth deformities of individual vertebrae that require apparatus for stabilization, and for muscular deformities of the spine that require apparatus for stabilization. Thus, deformities, as referred to herein, shall be understood to include all of the above-mentioned deformities.

What is claimed is:

1. A method for correcting scoliosis and rotational deformities of the spine by posterior surgical procedures, which method comprises:
   surgically exposing the spine posteriorly;
   hooking onto the cephalad side of a lamina of a first vertebra (170f) on one side of the spinous processes of said spine with a first hook (90f);
   hooking onto the caudad side of a lamina of a second vertebra (170e) on said one side of the spinous processes of said spine with a second hook (90e);
   hooking onto a first transverse process (184b) on said one side of said spinous processes of said spine of a third vertebra that is intermediate of said first and second vertebrae with a third hook (90h);
   applying a first force to said first (170f) and second (170e) vertebrae by changing the distance between said first (90f) and second (90e) hooks;
   applying a second force to said third vertebra that moves said first transverse process (184b) towards one (170f or 170e) of the other two said vertebrae, and that moves said first transverse process (184b) posteriorly thereby rotating said third vertebra;
   hooking onto a second transverse process (184a) on said one side of said spinous processes of said spine of a fourth vertebra that is intermediate of said second and third vertebrae; and
   applying a third force to said fourth vertebra that comprises moving said fourth vertebra away from said third vertebra and that moves said second transverse process (184a) posteriorly thereby rotating said fourth vertebra in the same direction as said third vertebra is rotated.

2. A method as claimed in claim 1 in which the first two said hooking steps comprise hooking into said laminae on the concave side of said scoliotic curve with respect to the spinous processes of said first and second vertebrae;
   said first force comprises a distraction force; and
   said first and second transverse processes are on said concave side of said scoliotic curve; whereby
   all three said forces cooperate to provide distraction forces to said concave side of said scoliotic curve.

3. A method as claimed in claim 2 in which said method further comprises:
   hooking onto one lamina of a vertebra (170a) that is proximal to the cephalad end of the scoliotic curve, on the cephalad side of the lamina, and on the side of the spinous process that is proximal to the convex side of the scoliotic curve, with a fifth hook (90a);
   hooking onto one lamina of a vertebra (170b) that is proximal to the caudad end of the scoliotic curve, on the caudad side of the lamina, and on the side of the spinous process that is proximal to the convex side of the scoliotic curve, with a sixth hook (90b); and applying a compression force to said convex side by decreasing the distance between said fifth (90a) and sixth (90b) hooks.

4. An apparatus (166a or 166b of FIG. 26) of the type used in the correction of spinal deformities by posterior surgical procedures, having an elongated member (72a or 72b of FIG. 26, or 72 of FIG. 9) with first (174a or 174b) and second (178a or 178b) ends and with a longitudinal axis (80 of FIG. 9), having a first hook (90a or 90e of FIG. 26, or 90 of FIGS. 15 and 16) that includes both a first attaching portion (100) and a first hooking portion (104) that is disposed around a first hook axis (106), having a second hook (90b or 90f of FIG. 26, or 90 of FIGS. 15 and 16) that includes both a second attaching portion (100) and a second hooking portion (104) that is disposed around a second hook axis (106), and having means for operatively attaching said first and second hooks (90) to said elongated member with said hooking portions (104) opening substantially toward opposite ones (174a and 178a, or 174b and 178b) of said ends of said elongated member (72a or 72b), and for longitudinally positioning one of said hooks (90) with respect to the other of said hooks (90), the improvement which comprises:

said means for operatively attaching said first hook (90) to said elongated member (72) comprises means (88 of FIGS. 9–14) for operatively attaching said first attaching portion (100) to said elongated member (72) at a radially spaced distance from said longitudinal axis (80), for permitting said first attaching portion (100) to move circumferentially (120 of FIG. 10) with respect to said longitudinal axis (80) at said radially spaced distance therefrom, and for permitting said first attaching portion (100) to move rotationally (118 of FIG. 10) about a pivot axis (116 of FIGS. 9–11) that is substantially parallel to longitudinal axis (80) and that is at said radially spaced distance from said longitudinal axis (80).

5. An apparatus (166a or 166b of FIG. 26) of the type used in the correction of spinal deformities by posterior surgical procedures, having an elongated member (72a or 72b of FIG. 26, or 72 of FIG. 9) with first (174a or 174b) and second (178a or 178b) ends and with a longitudinal axis (80 of FIG. 9), having a first hook (90a or 90e of FIG. 26, or 90 of FIGS. 15 and 16) that includes a first attaching portion (100), and that includes a first hooking portion (104) disposed around a first hook axis (106), having a second hook (90b or 90f of FIG. 26, or 90 of FIGS. 15 and 16) that includes a second attaching portion (100), and that includes a second hooking portion (104) disposed around a second hook axis (106), and having means for operatively attaching said first and second hooks (90) to said elongated member with said hooking portions (104) opening substantially toward opposite ones (174a and 178a, or 174b and 178b) of said ends of said elongated member (72a or 72b), and for longitudinally positioning one of said hooks (90) with respect to the other of said hooks (90), the improvement which comprises:

said means for operatively attaching said first hook (90) to said elongated member (72) comprises said first attaching portion (100) of said first hook (90), and a first carrier (88 of FIGS. 9–14);

said means for operatively attaching said first hook (90) to said elongated member (72) comprises said first attaching portion (100) of said first hook (90), and a first carrier (88 of FIGS. 9–14);

said first carrier (88 of FIGS. 9–14) includes a rod-receiving opening (92) being rotatably (120 of FIG. 10) disposed onto said elongated member (72 of FIGS. 9 and 10), and a socket (94) that is radially displaced from said rod-receiving opening (92) at a given distance; and said means for operatively attaching said first hook (90) to said elongated member (72) comprises means (102 of FIGS. 15 and 16) for attaching said attaching portion in said socket and for permitting said first attaching portion (100) to move rotationally (118 of FIG. 10) in said socket (94) about a pivot axis (116 of FIGS. 9–11) that is substantially parallel to said longitudinal axis (80).

6. An apparatus as claimed in claims 4 or 5 in which said attaching means (88) for said first hook (90) includes means (102+110+99) for permitting said first hooking portion (104) of said first hook (90) to pivot away from said elongated member (72) about an axis (122 of FIGS. 9–11) that is parallel to said first hook axis (106) and that intercepts said first attaching portion (100) of said first hook (90).

7. An apparatus as claimed in claims 4 or 5 in which said attaching means (88) for said first hook (90) includes means (102+110+99) for permitting said first hooking portion (104) to pivot at least 3 degrees each way from said longitudinal axis (80) about an axis (128 of FIGS. 9–11) that is orthogonal to said longitudinal axis (80) and that intersects both said longitudinal axis (80) and said pivot axis (116).

8. An apparatus as claimed in claims 4 or 5 in which said attaching means (88) for said first hook (90) includes means (102+110+99) for permitting said first hooking portion (104) of said first hook (90) to pivot away from said elongated member (72) about an axis (122 of FIGS. 9–11) that is parallel to said first hook axis (106) and that intercepts said attaching portion (100) of said first hook (90), and for permitting said first hooking portion (104) to pivot at least 3 degrees each way from said longitudinal axis (80) about an axis (128 of FIGS. 9–11) that is orthogonal to said longitudinal axis (80) and that intercepts both said longitudinal axis (80) and said pivot axis (116).

9. An apparatus as claimed in claims 4 or 5 in which said attaching means for said one hook (90) includes means, comprising a convex spherical surface (102) on said first attaching portion (100), for permitting said first hook to pivot about an axis (122 or 128 of FIGS. 9–11) that is orthogonal to said longitudinal axis (80) and that intercepts said socket axis (95).

10. An apparatus (166a or 166b of FIG. 26) of the type used in the correction of spinal deformities by posterior surgical procedures, having an elongated member (72a or 72b of FIG. 26, or 72 of FIG. 9) with first (174a or 174b) and second (178a or 178b) ends and with a longitudinal axis (80 of FIG. 9), having a first hook (90a or 90e of FIG. 26, or 90 of FIGS. 15 and 16) that includes a first attaching portion (100), and a first hooking portion (104) that is disposed around a first hook axis (106) and that opens toward said first attaching portion (100), having a second hook (90b or 90f of FIG. 26, or 90 of FIGS. 15 and 16) that includes a second attaching portion (100), and a second hooking portion (104) that is disposed around a second hook axis (106) and that opens toward said second attaching portion (100), and having means for operatively attaching said first and second hooks (90) to said elongated member with said hooking portions (104) opening substantially toward opposite ones (174a and 178a, or 174b and 178b) of said ends of said elongated member (72a or 72b), and for longitudinally positioning one of said hooks (90) with respect to the other of said hooks (90), the improvement which comprises:

said means for operatively attaching said first hook (90) to said elongated member (72) comprises said first attaching portion (100) of said first hook (90), and a first carrier (88 of FIGS. 9-14);

said first carrier (88 of FIGS. 9-14) comprises a body (89) having first (91) and second (93) end surfaces, having a rod-receiving opening (92) that is disposed along a second longitudinal axis (98), that opens through said end surfaces (92 and 93), and that is rotatably disposed onto said elongated member (72), having a socket (94) that is disposed along a socket axis (95) substantially parallel to and radially displaced from said second longitudinal axis (98), that opens through said first end surface (91), that extends longitudinally into said body (89), and that terminates in a socket surface (96), having a side surface (97) that interconnects said end surfaces (91 and 93) remote from said rod-receiving opening (92) and adjacent to said socket (94), and having a shank-receiving slot (99) that is disposed in a plane (123) that substantially includes both said second longitudinal axis (98) and said socket axis (95), and that opens into said socket (94) through said side surface (97) and through said end surfaces (91 and 93);

said first hook (90) includes a hook shank (110) that is disposed intermediate of said first attaching portion (100) and said first hooking portion (104) and that is freely disposed into said shank-receiving slot (99); and said first attaching portion (100) includes a convex spherical surface (102) that is juxtaposed against said first attaching portion (100) and that seats against said socket surface (96); whereby said convex spherical surface (102) of said first attaching portion (100) permits rotational movement of said first hook (90) about said socket axis (95); and whereby said convex spherical surface (102) of said first attaching portion (100) and said shank-receiving slot (99) of said first carrier (88) cooperate to permit pivotal movement of said first hook (90) about an axis (122 of FIGS. 9-11) that is substantially orthogonal to a plane that includes said second longitudinal axis (98) and said socket axis (95) and that substantially intercepts said socket axis (95).

11. An apparatus as claimed in claim 10 in which said attaching means (88) for said first hook (90) includes means (102+110+99) for permitting said first hooking portion (104) to pivot at least 3 degrees each way from said longitudinal axis (80) about an axis (128 of FIGS. 9-11) that is orthogonal to said longitudinal axis (80) and that intersects both said longitudinal axis (80) and said socket axis (95).

12. An apparatus as claimed in claims 4, 5, or 10 in which said elongated member (72) includes an externally threaded portion (73); and said means for longitudinally positioning said one hook (90) includes said threaded portion (73) and a threaded nut (76).

13. An apparatus (166a or 166b of FIG. 26) of the type used in the correction of spinal deformities by posterior surgical procedures, having an elongated member (72b of FIG. 26, or 72 of FIG. 9) with first (174a or 174b) and second (178a or 178b) ends and with a longitudinal axis (80 of FIG. 9), having a first hook (90a or 90e of FIG. 26, or 90 of FIGS. 15 and 16) that is operatively attached to said elongated member (72) at a first longitudinal position with respect to said longitudinal axis (80) and that opens substantially toward one of said ends, having a second hook (90b or 90f of FIG. 26 or 90 of FIGS. 9-11) that is operatively attached to said elongated member (72) and that opens substantially toward the other of said ends, and having means for longitudinally positioning one of said hooks (90) with respect to the other of said hooks (90), the improvement which comprises:

a third hook (90c, 90d, 90f, or 90h of FIG. 26, or 90 of FIGS. 15 and 16) having an attaching portion (100) and having a hooking portion (104) that is disposed around a hook axis (106); and means (88c, 88d, 182, or 183 of FIG. 26, or 88 of FIGS. 9-14, or 182 of FIGS. 29-31) for operatively attaching said third hook (90) to said elongated member (72) intermediate of said first and second hooks with said attaching portion (100) radially displaced from said longitudinal axis (80) for longitudinally positioning said third hook (90c, 90d, 90g, or 90h of FIG. 26) with respect to one of the other of said hooks (90a, 90b, 90e, or 90f of FIG. 26), for permitting said attaching portion (100) of said third hook (90) to move circumferentially with respect to said longitudinal axis (80) and one of the other of said hooks, and for permitting rotational movement of said third hook (90) about a pivot axis (116 or 122 of FIGS. 9-11) that is spaced from said longitudinal axis (80) and that intercepts said attaching portion.

14. An apparatus as claimed in claim 13 in which said pivot axis (116 of FIGS. 9-11) that is spaced apart from said longitudinal axis (80) is parallel to said longitudinal axis (80).

15. An apparatus as claimed in claim 13 in which said pivot axis (122) that is spaced apart from said longitudinal axis (80) is parallel to said hook axis (106).

16. An apparatus (166a or 166b of FIG. 26) of the type used in the correction of spinal deformities by posterior surgical procedures, having an elongated member (72b of FIG. 26, or 72 of FIG. 9) with first (174b) and second (178b) ends and with a longitudinal axis (80 of FIG. 9), having a first hook (90e of FIG. 26, or 90 of FIGS. 15 and 16) that is operatively attached to said elongated member (72) at a first longitudinal position with respect to said longitudinal axis (80) and that opens substantially toward one of said ends, having a second hook (90f of FIG. 26 or 90 of FIGS. 9-11) that is operatively attached to said elongated member (72) and that opens substantially toward the other of said ends, and having means for longitudinally positioning one of said hooks (90) with respect to the other of said hooks (90), the improvement which comprises:

a third hook (90g or 90h of FIG. 26, or 90 of FIGS. 15 and 16) having an attaching portion (100) and having a hooking portion (104) that is disposed around a hook axis (106); and means (182 or 183 of FIG. 26, or 182 of FIGS. 29-31) for operatively attaching said third hook (90) to said elongated member (72) intermediate of said first and second hooks with said attaching portion (100) radially displaced from said longitudinal axis (80), for longitudinally positioning said third hook (90g or 90h of FIG. 26) with respect to one of the other of said hooks (90e or 90f of FIG. 26), for permitting said attaching portion (100) of said third hook (90) to move circumferentially with respect to said longitudinal axis (80) and one of the other of said hooks, for permitting said third hook (90 of FIGS. 29-31) to be positioned in a hooking plane (193 of FIG. 29) that is at an angle of 15 to 45 degrees with respect to said longitudinal axis (80) as measured about a transverse axis (128 of FIGS. 29 and 30) that is orthogonal to said longitudinal axis (80) and that intercepts both said longitudinal axis (80) and said attaching portion (100) of said third hook (90), and for permitting said third hook (90) to pivot about a pivot axis (122 of FIG. 29) that is substantially parallel to said hook axis (106) and that intercepts said attaching portion.

17. An apparatus (166b of FIG. 26) of the type used in the correction of spinal deformities by posterior surgical procedures, having an elongated member (72b of FIG. 26, or 72 of FIG. 9) with first (174b) and second (178b) ends and with a longitudinal axis (80 of FIG. 9), having a first hook (90e of FIG. 26, or 90 of FIGS. 15 and 16) that is operatively attached to said elongated member (72) at a first longitudinal position with respect to said longitudinal axis (80) and that opens substantially toward one of said ends, having a second hook (90f of FIG. 26 or 90 of FIGS. 9-11) that is operatively attached to said elongated member (72) and that opens substantially toward the other of said ends, and having means for longitudinally positioning one (90e or 90f) of said hooks with respect to the other of said hooks, the improvement which comprises:

a third hook (90g or 90h of FIG. 26, or 90 of FIGS. 15 and 16) having an attaching portion (100), and having a hooking portion (104) that is disposed around a hook axis (106); and means (182 or 183 of FIG. 26, or 182 of FIGS. 29-31) for operatively attaching said third hook (90g or 90h of FIG. 26, or 90 of FIGS. 29-31) to said elongated member (72b of FIG. 26, or 72 of FIGS. 29-31) intermediate of said first (90e) and second (90f) hooks with said attaching portion radially displaced from said longitudinal axis (80), for longitudinally positioning said third hook with respect to one or the other (90e or 90f) of said hooks, for permitting said third hook (90 of FIGS. 29-31) to be positioned in a hooking plane (193 of FIG. 29) that is at an angle of 15 to 45 degrees with respect to said longitudinal axis (80) as measured about a transverse axis (80) and that intercepts both said longitudinal axis (80) and said attaching portion (100) of said third hook (90), for permitting said attaching portion (100) of said third hook (90) to move circumferentially with respect to said longitudinal axis (80) and one of the other of said hooks, and for permitting rotational movement of said third hook (90) about a pivot axis (116 of FIGS. 9-11) that lies in said hooking plane (193) and that intercepts said attaching portion (100).

18. An apparatus as claimed in claims 13, 16, or 17 in which said attaching means for said third hook (90) includes means, comprising a spherical surface (102) on said attaching portion (100) for permitting said third hook (90) to pivot about a second axis that intercepts said attaching portion (100).

19. An apparatus (116b of FIG. 26) of the type used in the correction of spinal deformities by posterior surgical procedures, having an elongated member (72b of FIG. 26, or 72 of FIG. 9) with first (174b) and second (178b) ends and with a longitudinal axis (80 of FIG. 9), having a first hook (90e of FIG. 26, or 90 of FIGS. 9-11) that is operatively attached to said elongated member (72) at a first longitudinal position with respect to said longitudinal axis (80) and that opens substantially toward one of said ends, having a second hook (90f of FIG. 26 or 90 of FIGS. 9-11) that is operatively attached to said elongated member (72) and that opens substantially toward the other of said ends, and having means for longitudinally positioning one (90e or 90f) of said hooks with respect to the other of said hooks, the improvement which comprises:

a third hook (90g or 90h of FIG. 26, or 90 of FIGS. 15 and 16) having an attaching portion (100), having a hooking portion (104) that is disposed around a hook axis (106) and that opens toward said attaching portion (100), and having a hook shank (110) that interconnects said attaching portion (100) and said hooking portion (104); and a carrier (182 or 183 of FIG. 26, or 182 of FIGS. 29-31) having a body that includes first and second end surfaces, having a rod-receiving opening (92 of FIG. 12) that is disposed along a longitudinal axis, that opens through said end surfaces, and that is rotatably disposed onto said elongated member (72), having a socket (94) radially disposed along a socket axis that is rotated from 15 to 45 degrees from said longitudinal axis (80) as measured about a transverse axis (128) that is orthogonal to said longitudinal axis (80) and that intercepts both said longitudinal axis (80) and said attaching portion (100), that opens through said first end surface, and that includes a socket surface (96) that is disposed intermediate of said end surfaces, and having means, comprising a slot in said carrier (182 or 183), for permitting said third hook (90) to pivot about a pivot axis (122) in a hooking plane (193) that includes said socket axis and said transverse axis (128).

20. An apparatus as claimed in claim 19 in which said attaching means for said third hook (90) includes means, comprising a spherical surface (102) on said attaching portion (100), for permitting said third hook to pivot about an axis that lies in said hooking plane (193) and that intercepts said attaching portion (100), and for permitting said hooking portion (104) to pivot at least 6 degrees about an axis (128 of FIGS. 29 and 30) that is orthogonal to said longitudinal axis (80) and that intercepts both said longitudinal axis (80) and said pivot axis (122).

21. An apparatus as claimed in claims 13, 16, 17, or 19 in which said attaching means for said third hook (90) includes means (102+110+99) for permitting said hooking portion (104) to pivot a total of at least 6 degrees about an axis (128 of FIGS. 9-11, or 128 of FIGS. 29 and 30) that is orthogonal to said longitudinal axis (80) and that intersects both said longitudinal axis (80) and said attaching portion (100).

22. An apparatus as claimed in claims 13, 16, 17, or 19 in which said elongated member (72) includes an externally threaded portion (73); and said means for longitudinally positioning said third hook (90) includes said threaded portion (73) and a threaded nut (76).

23. A method for use in correcting spinal deformities by posterior surgical procedures, which method comprises:

surgically exposing the spine posteriorly;

hooking first (90a or 90e) and second (90b or 90f) hooks onto respective ones of first and second vertebrae on one side of the spinous processes of said spine subsequent to said exposing step;

placing an elongated member (72a or 72b) having a longitudinal axis (80a or 80b) adjacent to said spine on said one side of said spinous processes subsequent to said exposing step;

pivotally attaching said first hook to said elongated member at a first longitudinal position thereof, at a radial distance therefrom, and at a first circumferential position in relation thereto;

operatively attaching said second hook to said elongated member at a second longitudinal position thereof;

longitudinally positioning one of said hooks with respect to the other of said hooks in the direction that applies a longitudinal force to said hooks; and pivoting said first hook about a pivot axis (116) that intercepts said pivotal attaching of said first hook and that is within 45 degrees of being parallel to said longitudinal axis.

24. A method for use in correcting spinal deformities by posterior surgical procedures, which method comprises:

surgically exposing the spine posteriorly;

hooking first (90a or 90e) and second (90b or 90f) hooks onto respective ones of first and second vertebrae on one side of the spinous processes of said spine subsequent to said exposing step;

assembling first (88a or 88e) and second (88b or 88f) carriers onto an elongated member (72a or 72b) that includes a longitudinal axis (80a or 80b);

placing said elongated member (72a or 72b) adjacent to said spine on said one side of said spinous processes;

pivotally attaching one of said hooks to one of said carriers at a radial distance from said elongated member and at a first circumferential position with relation thereto;

attaching the other one of said hooks to the other one of said carriers;

longitudinally positioning one of said carriers with respect to the other of said carriers in the direction that applies a longitudinal force to said hooks;

circumferentially positioning said pivotal attachment of said one hook about said longitudinal axis at said radial distance by rotationally positioning said one carrier; and pivoting said one hook about a pivot axis (116) that intercepts said pivotal attaching of said one hook and that is within 45 degrees of being parallel to said longitudinal axis.

25. A method for use in correcting signal deformities by posterior surgical procedures, which method comprises:

surgically exposing the spine posteriorly;

hooking first (90a or 90e) and second (90b or 90f) hooks onto respective ones of first and second vertebrae on one side of the spinous processes thereof subsequent to said exposing step;

placing an elongated member (72a or 72b) having a longitudinal axis (80a or 80b) adjacent to said spine on said one side of said spinous processes thereof;

operatively attaching said first hook to said elongated member at a first longitudinal position thereof and at a radial distance therefrom;

operatively attaching said second hook to said elongated member at a second longitudinal position thereof and at a radial distance therefrom;

longitudinally positioning one of said hooks with respect to the other of said hooks in the direction that applies a longitudinal force to one of said hooks;

circumferentially positioning said attaching of one of said hooks with respect to the other of said hooks about said longitudinal axis as a function of said longitudinal positioning, said hooking force, and resultant correction of said spinal deformities; and pivotally positioning said one hook about an axis (116, 122, or 128 of FIG. 9) that is diverse from said longitudinal axis (80) as a function of said positioning step and said longitudinal force.

26. A method as claimed in claim 25 in which said one hook (90) includes an attaching portion (100) and a hooking portion (104) that is disposed around a hook axis (106); and said axis (122) of said pivotal positioning is parallel to said hook axis and intercepts said attaching portion.

27. A method as claimed in claim 25, in which said one hook (90) includes an attaching portion (100); and said axis (128) of said pivotal positioning is orthogonal to said longitudinal axis (80) and intercepts both said longitudinal axis and said attaching portion.

28. A method as claimed in claim 25 in which said axis (116) of said pivotal positioning is substantially parallel to said longitudinal axis (80).

29. A method for use in correcting spinal deformities by posterior surgical procedures, which method comprises:

surgically exposing the spine posteriorly;

hooking a first hook (90e) onto a lamina of a first vertebra, on the caudad side, and on one side of the spinous processes, subsequent to said exposing step;

hooking a second hook (90f) onto a lamina of a second vertebra, on the cephalad side, and on said one side of said spinous processes, subsequent to said exposing step;

attaching said first and second hooks to an elongated member (72b) having a longitudinal axis;

hooking a third hook (90g or 90h) onto a transverse process (184a or 184b) that is intermediate of said first and second vertebrae and that is on said one side of said spinous processes;

pivotally attaching said third hook to said elongated member, at a radially spaced distance from said longitudinal axis, and with said third hook being in a hooking plane (193 of FIG. 29) that is at an angle (195) of 15 to 45 degrees with respect to said longitudinal axis;

longitudinally positioning one of said hooks with respect to another one of said hooks in the direction that provides a hooking force on said third hook;

circumferentially positioning (FIG. 38) said pivotal attaching of said third hook as a function of said hooking force (194 of FIGS. 33 and 37) on said third hook and said angle (195) of said hooking plane (193); and pivotally positioning said third hook about an axis (116, 122, or 128 of FIG. 9) that is diverse from said longitudinal axis (80), and that intercepts said pivotal attaching of said third hook, as a function of said longitudinal positioning step and said hooking force.

30. A method for use in correcting spinal deformities by posterior surgical procedures, which method comprises:

surgically exposing the spine posteriorly;

hooking a first hook (90e) onto a lamina of a first vertebra on the caudad side, and on one side of the spinous processes, subsequent to said exposing step;

hooking a second hook (90f) onto a lamina of a second vertebra, on the cephalad side, and on said one side of said spinous processes, subsequent to said exposing step;

hooking a third hook (90g or 90h) onto a transverse process (184a or 184b) that is intermediate of said first and second vertebrae and that is on said one side of said spinous processes;

assembling first (88e), second (88f), and third (182 or 183) carriers onto an elongated member (72b) that includes a longitudinal axis (80b);

attaching said first and second hooks to said first and second carriers respectively;

pivotally attaching said third hook to said third carrier, at a radial distance from said elongated member, and with said third hook in a hooking plane (193 of FIG. 29) that is at an angle (195) of 15 to 45 degrees with respect to said longitudinal axis;

longitudinally positioning one of said hooks with respect to another of said hooks in a direction that puts a hooking force onto said third hook;

circumferentially positioning (FIG. 38) said third carrier (182), and said pivotal attachment of said third hook, as a function of said hooking force (194 of FIGS. 33 and 37) on said third hook and said angle (195) of said hooking plane (193); and pivoting said third hook posteriorly as a function of said hooking force.

31. A method as claimed in claims 29 or 30 in which said method further comprises pivoting said third hook about an axis that lies in said hooking plane (193), as a function of said longitudinal positioning, said hooking force, and resultant correction of said spinal deformities.

32. A method as claimed in claims 23, 25, or 30 in which said elongated member (72) includes an externally threaded portion (73) and said longitudinal positioning includes helical positioning of threaded nuts (76).

33. A method for use in correcting spinal deformities by posterior surgical procedures, which method comprises:

surgically exposing the spine posteriorly;

hooking a first hook (90e) onto a lamina of the first vertebra, on the caudad side, and on one side of the spinous processes, subsequent to said exposing step;

hooking a second hook (90f) onto a lamina of a second vertebra, on the cephalad side, and on said one side of said spinous processes, subsequent to said exposing step;

attaching said first and second hooks to an elongated member (72b) having a longitudinal axis;

hooking a third hook (90e or 90h), that includes an attaching portion (100), onto a transverse process (184a or 184b) that in intermediate of said first and second vertebrae and that is on said one side of said spinous processes;

pivotally attaching said attaching portion to said elongated member, at a radially spaced distance from said longitudinal axis, and with said third hook being in a hooking plane (193 of FIG. 29) that is at an angle (195) of 15 to 45 degrees with respect to said longitudinal axis;

longitudinally positioning one of said hooks with respect to another one of said hooks in the direction that provides a hooking force on said third hook;

circumferentially positioning (FIG. 38) said pivotal attachment of said third hook as a function of said hooking force (194 of FIGS. 33 and 37) on said third hook and said angle (195) of said hooking plane (193); and pivoting said third hook (80), about an axis (128 of FIGS. 29 and 30) that orthogonally intercepts said longitudinal axis (80) and that intercepts said attaching portion (100), as a function of said longitudinal positioning, said hooking force, and resultant correction of said spinal deformities.

34. A method for use in correcting spinal deformities by posterior surgical procedures, which method comprises:

surgically exposing the spine posteriorly;

hooking a first hook (90e) onto a lamina of a first vertebra, on the caudad side, and one side of the spinous processes, subsequent to said exposing step;

hooking a second hook (90f) onto a lamina of a second vertebra, on the cephalad side, and on said one side of said spinous processes, subsequent to said exposing step;

hooking a third hook (90g or 90h), that includes an attaching portion (100), onto a transverse process (184a or 184b) that is intermediate of said first and second vertebrae and that is on said one side of said spinous processes;

assembling first (88e), second (88f), and third (182 or 183) carriers onto an elongated member (72b) that includes a longitudinal axis (80b);

attaching said first and second hooks to said first and second carriers respectively;

pivotally attaching said attaching portion of said third hook to said third carrier, at a radial distance from said elongated member, and with said third hook in a hooking plane (193 of FIG. 29) that is at an angle (195) of 15 to 45 degrees with respect to said longitudinal axis;

longitudinally positioning one of said hooks with respect to another of said hooks in a direction that puts a hooking force onto said third hook;

circumferentially positioning (FIG. 38) said third carrier (182), and said attaching portion, as a function of said hooking force (194 of FIGS. 33 and 37) on said third hook and said angle (195) of said hooking plane (193);

pivoting said third hook posteriorly, about an axis (122) that intercepts said attaching portion, as a function of said hooking force; and pivoting said third hook (90), about an axis (128 of FIGS. 29 and 30) that orthogonally intercepts said longitudinal axis (80) and that intercepts said attaching portion (100), as a function of said longitudinal positioning, said hooking force, and resultant correction of said spinal deformities.

* * * * *